US00PP36688P3

(12) United States Plant Patent
Volz et al.

(10) Patent No.: US PP36,688 P3
(45) Date of Patent: May 20, 2025

(54) APPLE TREE NAMED 'HOT125A1'

(50) Latin Name: *Malus domestica*
Varietal Denomination: HOT125A1

(71) Applicants: The New Zealand Institute for Plant and Food Research Limited, Auckland (NZ); Institut De Recerca I Tecnologia Agroalimentaries (IRTA), Barcelona (ES); FruitFutur A.I.E, Lledia (ES)

(72) Inventors: Richard Volz, Havelock North (NZ); Simo Alegre, Lleida (ES)

(73) Assignees: The New Zealand Institute for Plant and Food Research Limited, Auckland (NZ); Institut De Recerca I Tecnologia Agroalimentaries (IRTA), Barcelona (ES); FruitFutur A.I.E, Lleida (ES)

( * ) Notice: Subject to any disclaimer, the term of this patent is extended or adjusted under 35 U.S.C. 154(b) by 0 days.

(21) Appl. No.: 18/831,023

(22) Filed: May 1, 2024

(65) Prior Publication Data

US 2024/0373770 P1 Nov. 7, 2024

Related U.S. Application Data

(60) Provisional application No. 63/464,158, filed on May 4, 2023.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

(56) References Cited

PUBLICATIONS

U.S. Appl. No. 18/831,022, filed May 1, 2024.
U.S. Appl. No. 18/831,021, filed May 1, 2024.

*Primary Examiner* — Kent L Bell
(74) *Attorney, Agent, or Firm* — LEYDIG, VOIT & MAYER, LTD.

(57) ABSTRACT

A new and distinct apple variety is described. The variety results from crossing the apple varieties 'A101R10T175' (not patented) and 'A123R06T021' (not patented) in Havelock North, New Zealand. The fruit of the apple tree of this new variety have an attractive appearance characterized by its pink, red colour and it notable for its long storage life. This new variety has been named 'HOT125A1'.

3 Drawing Sheets

Genus and species plant named: *Malus domestica.*
Variety denomination: 'HOT125A1'.

BACKGROUND OF THE INVENTION

The new plant variety described herein resulted from a selection from a population of seedlings derived from the controlled crossing of the apple varieties 'A101R10T175' (not patented) (seed parent) and 'A123R06T021' (not patented) (pollen parent). The planned cross was made in 2003 on trees located in Havelock North, Hawke's Bay, New Zealand and the seed transported and sown in plots in Gimenells near Lleida, Catalonia, Spain. 'HOT125A1' was selected in 2010 as a single plant from among a population of seedlings and was selected for its attractive appearance, good flavor, texture and storage. It was asexually propagated first in Lleida, Spain by budding onto 'M9' rootstock (not patented). The variety has since been observed over three asexually propagated generations and found to remain true to type.

SUMMARY OF THE INVENTION

'HOT125A1' is characterized by its attractive fruit with good texture and flavor, harvesting in mid-September in Spain. Under growing conditions in Spain 'HOT125A1' is distinguished from other apple varieties due to the following unique characteristics: Compared to 'Fuji' (not patented), 'HOT125A1' has an earlier harvest season by approximately 6 weeks, and a significantly higher proportion of the skin surface is covered by over colour, 60%, compared to 'Fuji', 40-50%.

Under the growing conditions in Spain the new variety was able to be distinguished from its parents 'A101R10T175' and 'A123R06T021', by the following characteristics:

'A123R06T021' has red fruit over colour compared to 'HOT125A1' which exhibits pink fruit over colour.

'A101R10T175' has red fruit over colour compared to 'HOT125A1' which exhibits fruit with pink overcolour.

Asexual reproduction of this new variety by budding and grafting shows that the aforementioned characteristics are true to form and are established and transmitted through succeeding propagation. This is true of buds grafted onto 'M9' rootstocks.

BRIEF DESCRIPTION OF PHOTOGRAPHS

The accompanying photographs show typical specimens of the tree, foliage and fruit of the new variety as depicted in colors as nearly true as is reasonably possible to make the same in a colour illustration of this character.

DETAILED DESCRIPTION

Figure 1:
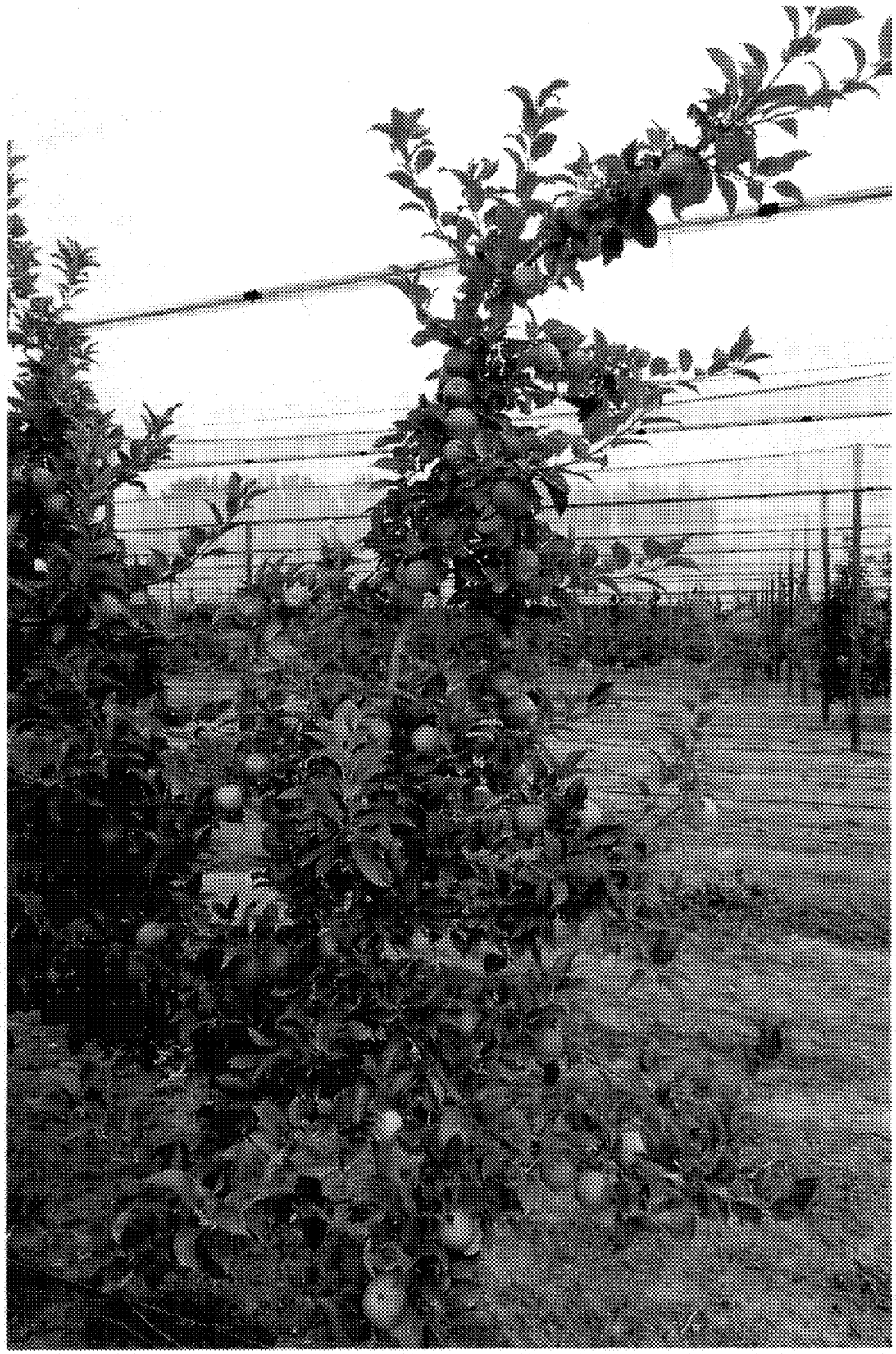
FIG. 1 shows a 3 year old tree of 'HOT125A1' scion on 'M9' rootstock in the field.
Figure 2:
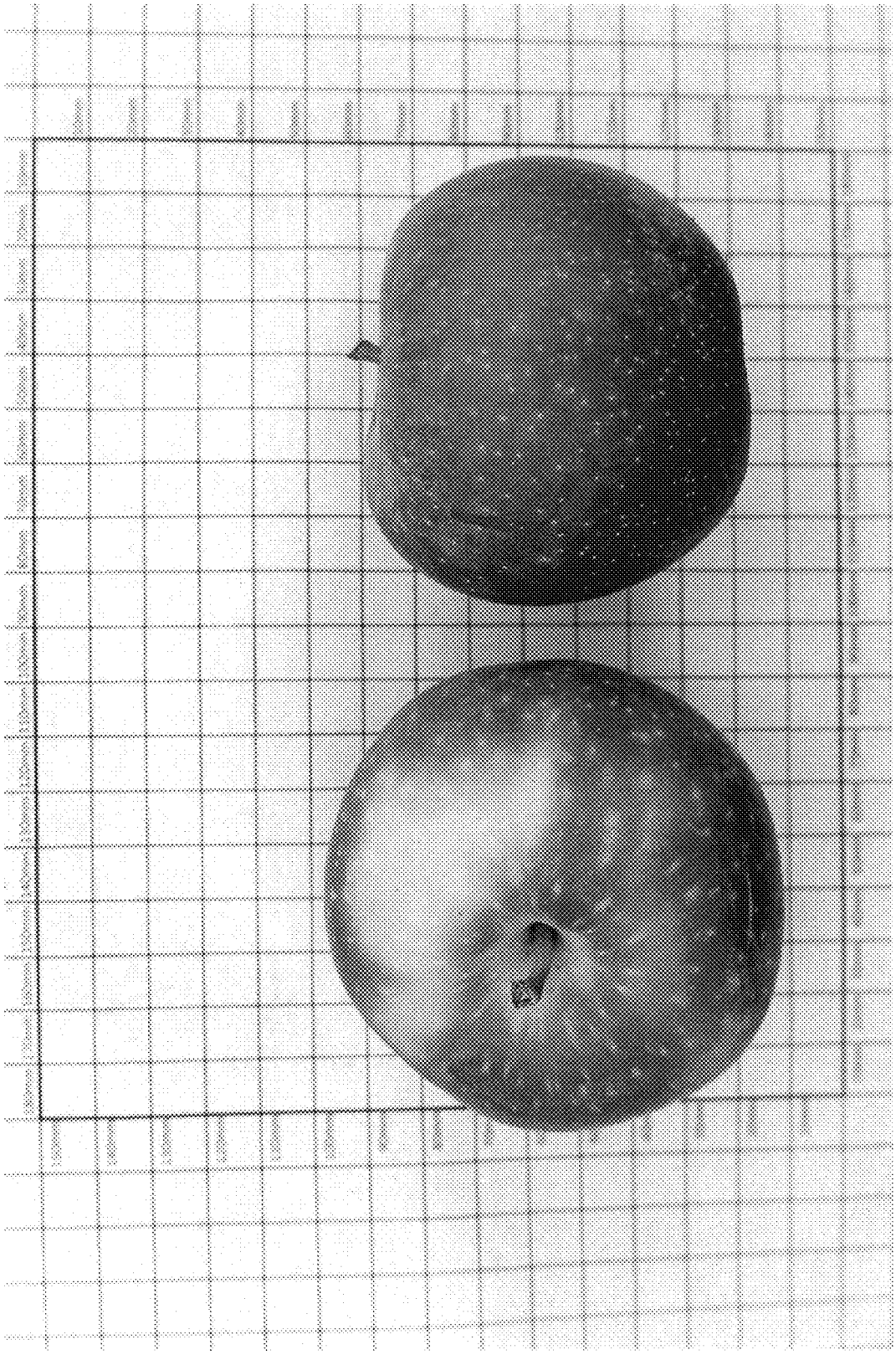
FIG. 2 shows whole 'HOT125A1' fruit.
Figure 3:
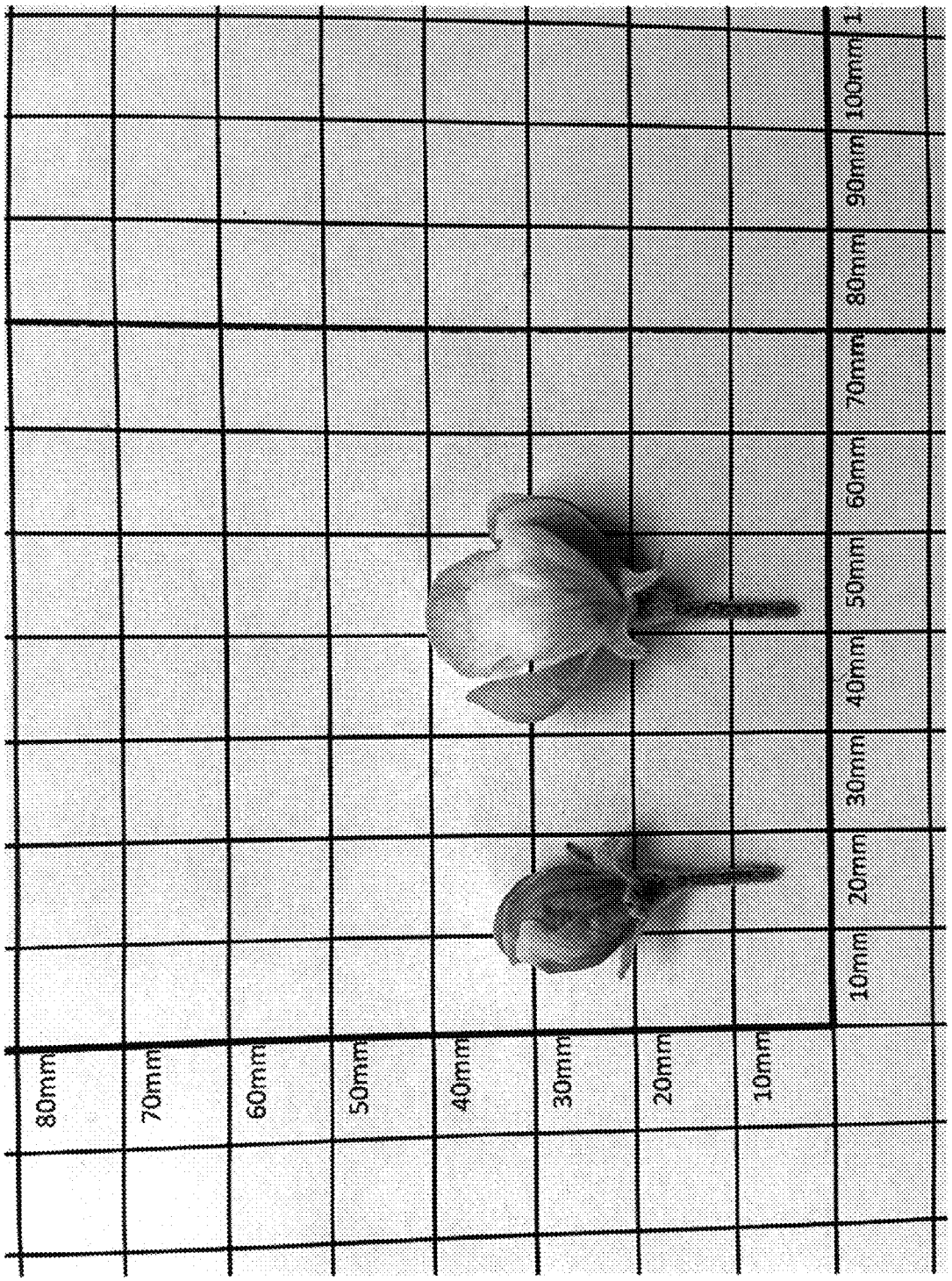
FIG. 3 shows 'HOT125A1' flower and bud.

The following is a description of the new variety with colour terminology in accordance with The Royal Horticultural Society Colour Charts (R.H.S.C.C.) sixth edition.

The specimens described were grown at Lleida, Catalonia, Spain. The observations were made over several seasons from 2017-2021 on 5-9 year old trees.

Tree: Ramified growth habit, approximately 2.35 m tall and 1.3 m wide; drooping habit; bearing on spurs and long shoots; medium vigor on 'M9' rootstock, managed under standard orchard practice.

Trunk: Measurements were taken 20 cm from the graft union. Trunk circumference approximately 18 cm; colour dark greyish yellow 199D; bark texture fine rough texture.

One year old shoot: Approximately 19.5 cm long, thin with straight growth; colour on the sunny side near greyish reddish brown 200B; average internode length 3.33 cm; number of lenticels were sparse, elongated in shape and pale orange yellow 159C and approximately 1 mm long and 0.66 mm wide.

Leaves: Average length 72.12 mm; average width 41 mm at the widest point; upper side of the blade near moderate olive green 147A; underside moderate yellow green 147B with absent or weak pubescence; basal shape truncate; apex shape acute; overall shape obovate; margin of the leaves serrate; the attitude in relation to the shoot upwards. Vegetative bud burst early March.

Petiole: Average length 17.31 mm; average width 2 mm; colour moderate yellow green 143D on the upper side; under side colour of the petiole brilliant yellow green 142B.

Stipule: Average length 6.34 mm; average width 0.45 mm; shape small and narrow; shape of apex acute; colour near light yellow green 154D on the upper side; under side colour of the stipules near light yellow green 154D.

Flowers: Colour at balloon stage strong purplish pink 63C; diameter of the open flower approximately 35.4 mm; flower shape is rounded; petals margins touching, and there were five flowers per cluster; time of beginning of flowering early April, followed by full bloom on the approximately 7th April.

Petals: Five petals per flower with a broad ovate shape; average length 16.15 mm; average width 11.59 mm; with a truncate base; petal margin is touching; lower surface colouration light purplish pink 63D with strong purplish red 63B veins.

Stamen: Average of 20 per flower. Filaments greenish white 155C and average length 8.85 mm. Anthers average length of 2.78 mm; average width 1.37 mm; colour light yellow 11B. Pollen colour brilliant greenish yellow 3A. Anther position below stigma.

Carpel: Pistil average length 5.96 mm; Pistil colour brilliant yellow green 149B.

Pedicel: Average length 21.72 mm; average diameter 1.26 mm; colour strong yellow green 145A.

Sepals: Five sepals per flower; overall shape of an acute and curved triangle; smooth margin; average length 8.03 mm; average width 3.9 mm; colour strong yellow green 144A on both upper and lower surface.

Fruit size: Large to very large; average width 82.6 mm; average height 74 mm; average weight 255 g.

Shape: Globose; position of maximum diameter middle; crowning at calyx end strong. Eye basin average depth 5.26 mm; average width 16.5 mm.

Skin: Chewy texture; ribbing absent or weak; bloom of skin strong; greasiness of skin moderate; background colour light greenish yellow 5D; number of lenticels many; size of lenticels medium.

Overcolour: Approximately 60% of skin surface; deep yellowish pink 46D; pattern of overcolour flush and mottled; width of stripes NA; absent or small amount of russet around stalk cavity; amount of russet on cheeks absent or small; area of russet around eye basin absent or small.

Stalk: Average length 23.6 mm; average width 2.53 mm; curvature weak. Average depth of stalk cavity 24.03 mm; average width 42.03 mm.

Flesh: Firm, average fruit firmness 8.4 kgf; very juicy; pale yellow 11D.

Flavor: Subacid, low flavor, nutty; soluble solids 13.7%.

Seeds: Five locules; medium seed size; average length 8.24 mm; average width 4.4 mm; colour moderate brown 165A.

Harvest: Mid-September.

Use: Dessert. Adapted to hot climate growing conditions. Earlier harvest and more distinctive colour than 'Fuji'.

Keeping quality: Excellent, up to 8 months at 0.5° C.+1 week shelf life.

Productivity is 10 kg/tree.

The invention claimed is:

1. A new and distinct variety of apple tree named 'HOT125A1' substantially as illustrated and described herein.

* * * * *